US00PP29802P2

(12) United States Plant Patent
Wood

(10) Patent No.: US PP29,802 P2
(45) Date of Patent: Nov. 6, 2018

(54) ***SYRINGA* PLANT NAMED 'SMNJRPI'**

(50) Latin Name: ***Syringa* hybrid**
Varietal Denomination: SMNJRPI

(71) Applicant: Timothy Wood, Spring Lake, MI (US)

(72) Inventor: Timothy Wood, Spring Lake, MI (US)

(73) Assignee: Spring Meadow Nursery, Inc, Grand Haven, MI (US)

( * ) Notice: Subject to any disclaimer, the term of this patent is extended or adjusted under 35 U.S.C. 154(b) by 0 days.

(21) Appl. No.: 15/732,481

(22) Filed: Nov. 20, 2017

(51) Int. Cl.
*A01H 5/02* (2018.01)

(52) U.S. Cl.
USPC ..... Plt./248
CPC ..... *A01H 5/02* (2013.01)

(58) Field of Classification Search
USPC ..... Plt./248
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Syringa* cultivar named 'SMNJRPI' is disclosed, characterized by distinctive pink flowers on plants with re-blooming characteristics. The new variety is a *Syringa* normally produced as an outdoor garden or container plant.

2 Drawing Sheets

Latin name of the genus and species: *Syringa* hybrid.
Variety denomination: 'SMNJRPI'.

BACKGROUND OF THE INVENTION

The present invention comprises a new and distinct variety of *Syringa*, hereinafter referred to by the cultivar name 'SMNJRPI'. This new *Syringa* was developed through a breeding program in Grand Haven, Mich. The objective of the breeding program was to develop new *Syringa* reblooming varieties in different flower colors. 'SMNJRPI' is an internal advanced selection from an in-house breeding program. The seed parent is an unnamed, unpatented proprietary breeding line. The pollen parent is unidentified as the new variety was produced through an open pollination breeding program. The open pollination resulting in the new variety was made in 2010. Selection of the new variety was made during 2013.

The first asexual propagation of 'SMNJRPI' was carried out during 2013 by softwood cuttings at a commercial nursery in Grand Haven, Mich. 'SMNJRPI' has been found to retain its distinctive characteristics through successive asexual propagations. Multiple generations have been asexually propagated, with the new variety characteristics reproduced true to type.

SUMMARY OF THE INVENTION

The following are the most outstanding and distinguishing characteristics of this new cultivar when grown under standard horticultural practices at Grand Haven, Mich.:

1. Pink flowers.
2. Reblooming flowering habit.

COMPARISON WITH THE PARENT VARIETIES

'SMNJRPI' is similar to the seed parent, in most horticultural characteristics. 'SMNJRPI' however differs in the following:

1. New variety has pink flowers, the seed parent has lavender flowers.
2. New variety has darker green foliage, seed parent has lighter green foliage.

COMMERCIAL COMPARISON

'SMNJRPI' is similar to the commercial variety *Syringa* 'Pink Perfume', U.S. Plant Pat. No. 24,252, in most horticultural characteristics. 'SMNJRPI' however differs in the following:

1. Plants of the new variety produce darker pink flowers, this comparator produces light pink flowers.
2. New variety has pink buds, comparator has magenta buds.

DESCRIPTION OF THE PHOTOGRAPHS

This new *Syringa* is illustrated by the accompanying photographs which show the plant's form, foliage and inflorescences. The colors shown are as true as can be reasonably obtained by conventional photographic procedures. Plants were grown in Grand Haven, Mich.

Figure 1:
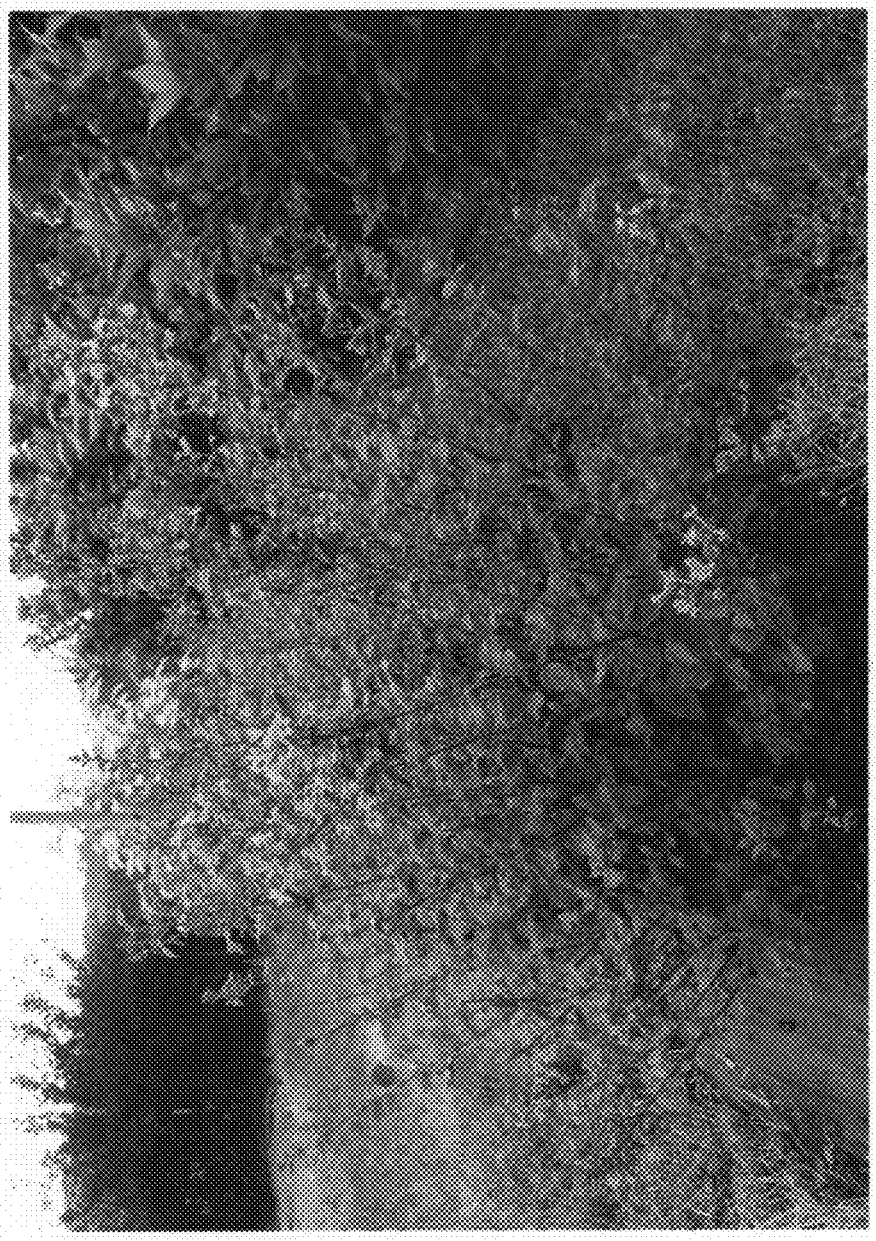

FIG. 1. Shows a flowering plant of 'SMNJRPI' in the ground at approximately 3 years old during Summer.

Figure 2:
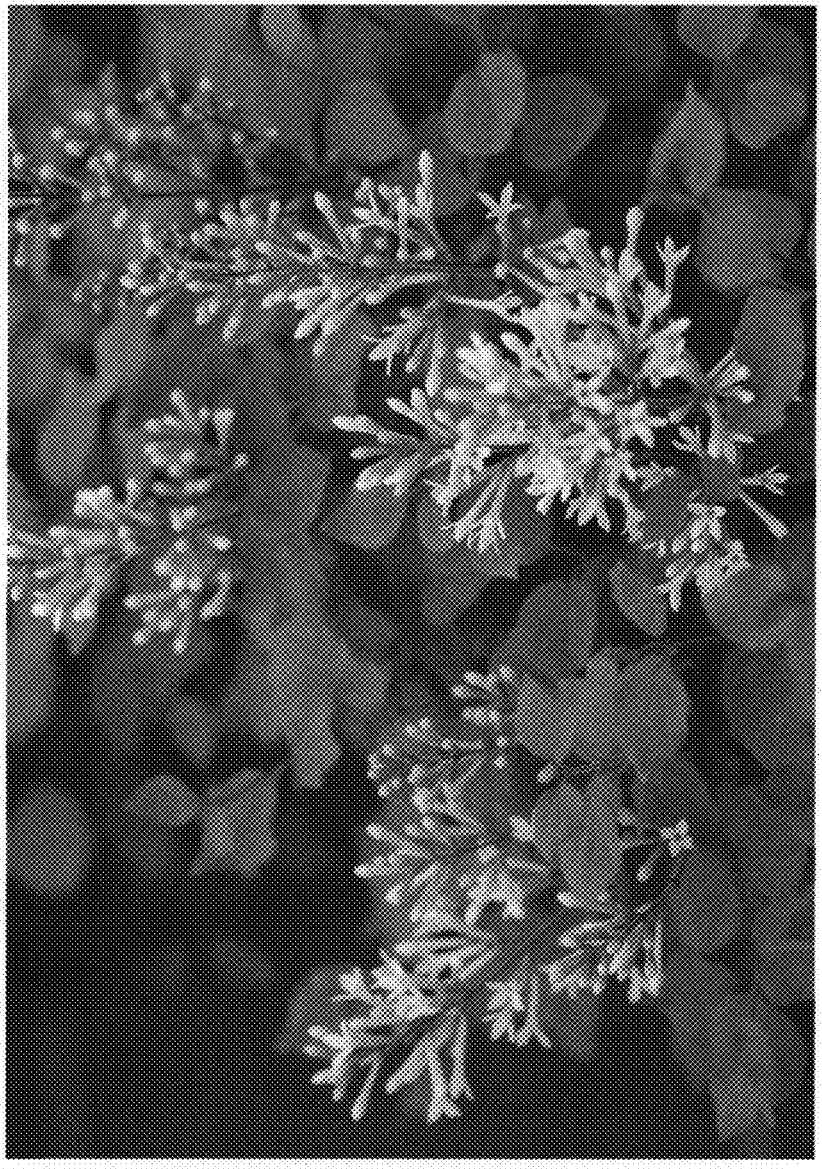

FIG. 2. Shows a close-up view of the inflorescence.

DESCRIPTION OF THE NEW CULTIVAR

In the following description, color references are made to The Royal Horticultural Society Colour Chart 2015 except where general terms of ordinary dictionary significance are used. The following observations and measurements describe 'SMNJRPI' plants grown in a poly-greenhouse during Summer, in Grand Haven, Mich. USA. The growing temperature ranged from 18° C. to 27° C. during the day and from 5° C. to 10° C. during the night. General light conditions are natural sunlight. Measurements and numerical values represent averages of typical plant types.

DETAILED BOTANICAL DESCRIPTION

Botanical classification: *Syringa* hybrid 'SMNJRPI'.
Propagation:
Typical method: Softwood cuttings.
Time to initiate rooting: About 20 days at approximately 18° C. to 27° C.
Time to produce a rooted young plant: About 3 months at approximately 18° C. to 27° C.
Root description: Dense, free branching, thin, fibrous. Colored tan, not accurately measured with an R.H.S. chart.
Plant description:
*Age of plant described.*—About 2 years in a 3 gallon container.
*Growth habit.*—Perennial shrub. Rounded.
*Height.*—60 cm in a 3 gallon container.
*Width.*—65 cm in a 3 gallon container.
*Growth rate.*—Good.
*Typical commercial container sizes.*—1, 2, and 3 gallon.
Branches:
*Branching habit.*—Freely branching.
*Lateral branch quantity.*—7.
*Lateral branch length.*—27 cm.
*Lateral branch diameter.*—2 mm.
*Branch angle.*—0-90 degrees.
*Branch strength.*—Strong.
*Branch color.*—Greyed-Brown 199B.
*Internode length.*—2 cm.
Foliage:
Leaves:
*Arrangement.*—Opposite.
*Length.*—2.4 cm.
*Width.*—1.7 cm.
*Shape.*—Ovate.
*Apex.*—Acute.
*Base.*—Obtuse.
*Margin.*—Entire.
*Texture upper surface.*—Slightly rough, pubescent.
*Texture lower surface.*—Slightly rough, pubescent.
*Color.*—Immature: Upper: Mostly Green 137 C with greyed purple 183 C around the edges. Lower: Partly Green 137 C with greyed purple 183 C near the bottom. Mature: Upper: Green 137B. Lower: Yellow Green 144A. Fall foliage color: Upper: Between Yellow-Green 151A and 151B. Lower: Near Greyed-Yellow 160C.
Venation:
*Color.*—Upper: Green white 157B. Lower: Green white 157B.
Petiole:
*Length.*—5 mm.
*Width.*—1 mm.
*Texture.*—Some pubescence.
*Color.*—Upper side: Greyed-orange 166B. Under side: Greyed-orange 177D.
Inflorescence:
*Description.*—Salverform flowers arranged in panicles.
*Flowering season.*—Spring to Mid-Summer.
*Fragrance.*—Light and sweet.
*Number of flowers per inflorescence.*—25-75.
*Inflorescence height.*—9-9.5 cm.
*Inflorescence diameter.*—6-8 cm.
Flowers:
*Flower diameter.*—6 mm.
*Flower depth.*—1.2 cm.
*Flower throat diameter.*—2 mm.
*Flower tube diameter (base).*—2 mm.
*Flower tube length.*—1 cm.
*Flower angle.*—Upward and outward.
*Persistence.*—Self-Cleaning.
Flower bud:
*Length.*—8 cm.
*Diameter.*—2 mm.
*Shape.*—Obovate.
*Color.*—About 50/50 mix of Red purple 62D and Red-Purple 64 A.
Petals:
*Number.*—4-6.
*Arrangement.*—Rotate.
*Length.*—4 mm.
*Width.*—2 mm.
*Shape.*—Ovate.
*Apex.*—Acute, slightly cupped.
*Margin.*—Entire.
*Texture.*—Smooth.
*Color.*—Immature upper surface: Purple 75D. Immature lower surface: Purple 75D. Mature upper surface: Purple 75D. Mature lower surface: Purple 75D. Flower tube (interior): Mix of Purple 75D and Red purple 67A. Flower throat (exterior): Purple 75D.
Sepals: Extremely minute (less than 1 mm by 1 mm in size) and inconspicuous.
Peduncle:
*Length.*—3 cm.
*Width.*—1 mm.
*Color.*—Green 183A.
*Texture.*—Smooth, pubescent.
*Angle.*—Upright/outward.
*Strength.*—Moderate.
Pedicels:
*Length.*—3-5 mm.
*Diameter.*—1 mm.
*Texture.*—Smooth, pubescent.
*Color.*—Green 183A.
*Strength.*—Good.
*Angle.*—Upright/outward.
Reproductive organs:
Gynoecium:
*Pistil number.*—1.
*Pistil length.*—3 mm.
*Stigma shape.*—Oblong to rounded.
*Stigma color.*—Close to White 155A.
*Style length.*—About 2 mm.
*Style color.*—Close to White 155A.
Androecium:
*Stamen number.*—2.
*Filament length.*—1.5 mm.
*Filament color.*—Grey 201A.
*Anther shape.*—Oblong.
*Anther length.*—2 mm.
*Anther color.*—Grey 201A.
*Amount of pollen.*—Some.
*Pollen color.*—Green-Yellow 1A.

OTHER CHARACTERISTICS

Fruit: Not observed to date.

Disease and insect resistance: No significant disease or pest resistance nor susceptibility have been observed.

Temperature range: Observed to tolerate temperatures between −33° C. and 36° C.

What is claimed is:

1. A new and distinct *Syringa* plant named 'SMNJRPI' as illustrated and described herein.

* * * * *